United States Patent [19]

Pearson et al.

[11] 3,950,424
[45] Apr. 13, 1976

[54] AROMATIC AMINE INHIBITED BY ANTIOXIDANTS AND METAL COMPLEXERS

[75] Inventors: Ronald L. Pearson, Cincinnati, Ohio; Charles A. Schneider, Villa Hills, Ky.

[73] Assignee: The Sherwin-Williams Company, Cleveland, Ohio

[22] Filed: Oct. 29, 1974

[21] Appl. No.: 518,531

[52] U.S. Cl. ............... 260/575; 260/576; 252/401; 252/402
[51] Int. Cl.² ................. C07C 87/50; C07C 87/52
[58] Field of Search ............ 260/575; 252/401, 402

[56] References Cited
UNITED STATES PATENTS

| | | | |
|---|---|---|---|
| 1,947,578 | 2/1934 | Bond et al. | 260/575 X |
| 1,973,724 | 9/1934 | Perkins et al. | 260/575 |
| 2,544,772 | 3/1951 | Audrieth | 252/401 UX |
| 2,655,543 | 10/1953 | Linch | 260/576 |
| 2,691,681 | 10/1954 | Linch | 260/575 |
| 3,728,281 | 4/1973 | Marks et al. | 260/575 X |

*Primary Examiner*—Allen B. Curtis
*Attorney, Agent, or Firm*—Neil A. DuChez; Richard G. Smith; James V. Tura

[57] ABSTRACT

A composition consisting of (A) an aromatic amine of the formula R—NH$_2$ wherein R is a monosubstituted or disubstituted phenyl radical in which one substituent group is an alkoxy group of 1 to 4 carbon atoms in one of the positions ortho and para to the NH$_2$ group and the other substituent is an alkyl group of 1 to 4 carbon atoms or a chlorine atom in any position on the benzene ring, the former substituent group is present when the radical is both monosubstituted and disubstituted while the latter substituent is present only when the radical is disubstituted, (B) from about 0.001 to about 0.20 percent by weight of a heterocyclic compound containing 2 to 8 carbon atoms, 2 to 3 sulfur atoms, 1 to 2 heterocyclic nitrogen atoms, at least 2 hydrogen atoms and a single heterocyclic ring with 2 or more carbon atoms, 1 to 2 nitrogen atoms and 1 to 2 sulfur atoms with the substituents on the nitrogen atoms being restricted to hydrogen atoms, and (C) from about 0.001 to about 0.02 percent by weight of a metal complexing agent selected from the group consisting of aliphatic, cyclicaliphatic and aromatic compounds of no more than about 22 carbon atoms and containing at least two carboxyl groups.

This invention also comprises the composition consisting of components (A), (B) and (C) combined with (D) from about 0.05 to about 0.5 percent by weight of a compound selected from the group consisting of compounds of the formula R'R''N—NH$_2$ and R'NH—NHR'' wherein R' and R'' can be the same or different and are selected from the group consisting of hydrogen atoms and alkyl groups of 1 to 4 carbon atoms.

9 Claims, No Drawings

3,950,424

AROMATIC AMINE INHIBITED BY ANTIOXIDANTS AND METAL COMPLEXERS

BACKGROUND OF THE INVENTION

1. Field of the Invention

The field of our invention comprises inhibited aromatic amines: More particularly, alkoxy aromatic amines inhibited by the synergistic effect resulting from the incorporation of anti-oxidants and metal complexers.

2. Description of the Prior Art

The most pertinent prior art known to us comprises the U.S. Pat. Nos. 2,691,681 and 2,655,543 issued to Linch. Both patents disclosed the stabilization of certain aromatic amines by the addition of stabilizers having heterocyclic structures. Neither disclosed or suggested, the synergistic effect produced by our invention.

Six other patents of relatively less pertinence are U.S. patent to Linch, U.S. Pat. Nos. 2,686,809; 2,757,197 and 2,763,689; U.S. Pat. No. 2,544,772 to Audrieth; U.S. Pat. No. 2,848,501 to Lloyd; and British Pat. No. 1,198,929 to Ripley.

Nothing in the prior art suggests our compositions or their advantages.

SUMMARY OF THE INVENTION

Our invention comprises the composition consisting essentially of the mixture of (A) an aromatic amine of the formula R—$NH_2$ wherein R is a monosubstituted or disubstituted phenyl radical in which one substituent is an alkoxy group of 1 to 4 carbon atoms in one of the positions ortho and para to the $NH_2$ group and the other substituent is an alkyl group of 1 to 4 carbon atoms or a chlorine atom in any position on the benzene ring, the former substituent group is present when the radical is both monosubstituted and disubstituted while the latter substituent is present only when the radical is disubstituted, (B) a heterocyclic compound containing 2 to 8 carbon atoms, 2 to 3 sulfur atoms, 1 to 2 heterocyclic nitrogen atoms, at least 2 hydrogen atoms andn a single heterocyclic ring with 2 or more carbon atoms, 1 to 2 nitrogen atoms and 1 to 2 sulfur atoms, the substituents on the nitrogen atoms being restricted to hydrogen atoms, the concentration of component (B) ranging from about 0.001 to about 0.20 percent by weight of component (A), and (C) a metal complexing agent selected from the group consisting of aliphatic, cyclicaliphatic and aromatic compounds of no more than about 22 carbon atoms, more preferably no more than about 12 carbon atoms, and containing at least two carboxyl groups, the concentration of component (C) ranging from about 0.001 to about 0.02 percent by weight of component (A).

Our invention also comprises the composition consisting essentially of the mixture of components (A), (B) and (C) with (D) a compound selected from the group consisting of compounds of the formulas R'R'λ'N—$NH_2$ and R'NH—NHR'', wherein R' and R'' can be the same or different and are selected from the group consisting of hydrogen atoms and alkyl groups of 1 to 4 carbon atoms, the concentration of component (D) ranging from about 0.05 to about 0.5 percent by weight of component (A).

An object of this invention is to provide a particular class of aromatic amines with properties of ambient color stability superior to the prior art. Other objects will become apparent from our description of the preferred embodiments.

DESCRIPTION OF THE PREFERRED EMBODIMENTS

We have discovered that alkoxy aromatic amines having the structure of component (A) exhibit significantly long "effective ambient white lifetimes" when incorporated with small proportions of inhibitors having the structure of component (B) mixed with inhibitors having the structures of component (C), or the combination of components (C) and (D).

When exposed to excessive heat and light, and to air and metallic surfaces, amines having the structure of component (A), in time, undergo significant color formation progressing from very light yellow, to light yellow, to very light brown, to light brown, to brown, to deep brownish red. When the amines have surpassed the "very light brown" stage, they are generally unacceptable for many uses, particularly as intermediates for azo dyes and various industrial chemicals. Purification processes are, for the most part, prohibitively costly and impractical. The coordination of processes producing the amines on the one hand, and processes using them on the other, is also in many instances impractical, particularly when the producer is not the user.

The term effective ambient white lifetime, as employed herein, is the time needed for an amine, stored at the ambient temperature and exposed to air, to reach the very light brown stage of color formation.

Typical examples of component (A) include 2-methoxy-3-methyl aniline; 2-methoxy-5-methyl aniline; 2-methyl-4-methoxy aniline; 5-methyl-4-methoxy aniline; 2-methoxy-4-chloro aniline; 2-methoxy-6-chloro aniline; 2-chloro-4-methoxy aniline; 5-chloro-4-methoxy aniline; 2-ethoxy-5-methyl aniline; 2-ethoxy-5-ethyl aniline; 2-ethoxy-5-chloro aniline; 5-amino-o-cresol isopropyl ether; ortho-anisidine; and para-anisidine.

As presently understood, the progressive color formation in component (A) is caused by the formation of oxidation products resulting from its contact with air, and by its contact with various metals that catalyze the color formation mechanism. Excessive heat and light tend to increase the rate of the color forming reactions.

Component (B) acts primarily as an antioxidant, but in some instances also functions as a metal complexer. The concentration of component (B) in component (A) ranges from about 0.001 to about 0.20 percent by weight, and preferably from about 0.005 to about 0.02 percent. Typical examples of component (B) include 2-thiazoline-2-thiol; 2,5-dimercapto-1,3,4-thiadiazole; 5,5-dimethyl-2-thiazoline-2-thiol; 5,6-dihydro-4,6,6-trimethyl-1,3,4H-thiazine-2-thiol; and 2-mercapto benzothiazole.

Component (C) acts primarily as a metal complexer and when combined with mixtures of components (A) and (B) induces a synergistic effect extending the effective ambient white lifetime of the mixture of components (A), (B) and (C) beyond the sum of the lifetimes experienced by the mixtures of components (A) and (B), and (A) and (C). The concentration of component (C) ranges from about 0.001 to about 0.02 percent by weight of component (A), and preferably from about 0.005 to about 0.015 percent. Typical examples of component (C) include oxalic acid; aurintricarboxylic acid; citric acid; phthalic acid; nitrilotriacetic acid;

pyridine-2,6-dicarboxylic acid; succinic acid; tartaric acid; 1,2-diaminocyclohexane-N,N,N',N'-tetraacetic acid; and N'-(2-hydroxyethyl)ethylenediamine-N,N,N'-triacetic acid.

Metals effectively complexed by compounds having the structure of components (B) or (C) include silver, aluminum, barium, beryllium, calcium, cadmium, cerium, cobalt, copper, europium, iron II, iron III, lanthanum, magnesium, manganese, neodymium, nickel, lead, praseodymium, strontium, yitrium and zinc.

Component (D) acts primarily as an antioxidant and when combined with mixtures of components (A), (B) and (C) induces a synergistic effect extending the effective ambient white lifetime of the mixture of components (A), (B), (C) and (D) beyond the sum of the lifetimes experienced by the mixtures of components (A) and (B), and (A) and (C), and (A) and (D). The concentration of component (D) ranges from about 0.05 to about 0.5 percent by weight of component (A), and preferably from about 0.05 to about 0.2 percent. Typical examples of component (D) include hydrazine; methyl hydrazine; ethyl hydrazine; n-propyl hydrazine; isopropyl hydrazine; n-butyl hydrazine; sec-butyl hydrazine; iso-butyl hydrazine; tert-butyl hydrazine; 1,1-dimethyl hydrazine, 1-methyl-1-ethyl hydrazine; 1-methyl-1-isopropyl hydrazine; 1-methyl-1-isobutyl hydrazine; 1,1-ethyl hydrazine; 1-ethyl-1-isopropyl hydrazine; 1-ethyl-1-isobutyl hydrazine; 1,2-dimethyl hydrazine; 1-methyl-2-ethyl hydrazine; 1-methyl-1-isopropyl hydrazine; 1-methyl-2-isobutyl hydrazine; 1-ethyl-2-isopropyl hydrazine; 1-ethyl-2-isobutyl hydrazine; and 1-isopropyl-2-isobutyl hydrazine.

Not all inhibitors having the structure of components (B), (C) and (D) work equally effective with each compound having the structure of component (A). The particular inhibitors selected depend upon the particular amine with which they are to be employed, the degree of color inhibition required, and the environment to which the amine is to be exposed. For example, excessive light and high temperature enhance color formation and so under such conditions high concentrations of the inhibitors will be required. Also, contact with oxygen and various metals enhance color formation and accordingly, the extent of air exposure the amines are to receive, the type and composition of containers they are to be stored in, and the equipment they are to be processed with, effect the selection and concentration of the inhibitors.

Optimum inhibition is obtained by adding the inhibitors to the amine as soon as it is prepared. Where the amine is distilled, maximum inhibition will be obtained by distilling the amine into a receiver containing the inhibitors, thereby avoiding unnecessary contact with air. When operating the distillation process at subatmospheric pressures, however, this is not always possible, due to the volatility of some of the inhibitors; hydrazine, for example, must be added at atmospheric or near-atmospheric pressures. It should be understood that our inhibitors can also be added during the manufacture of the amines and, in particular, to crude amines before crystallization to inhibit color formation during drying.

The inhibitors can be added to amines in the liquid form by simply dissolving them. They can be added to amines in the solid form by melting the amine or dissolving it in an inert liquid and then mixing the inhibitors into the amine and dissolving them. If the inhibitors are not soluble in the amine to the extent desired, they can be added as a solution by first dissolving them in a suitable liquid solvent such as an alcohol or an ether.

The following example is intended to illustrate our invention and is not intended to limit or impair the scope of the claims.

EXAMPLE

Samples of crude para-cresidine (2-methoxy-5-methylaniline) were distilled at reduced pressures in the range of 14 to 16 mmHg absolute and at corresponding temperatures in the range of 123°C to 125°C to obtain nearly colorless, molten products for studying the prevention of color formation. The inhibitors were added in sufficient quantities to produce the indicated concentrations while the samples were stirred and maintained at temperatures in the range of about 55°C to 65°C and, except for hydrazine, at the above reduced pressures. Hydrazine, due to its volatility, was added at atmospheric pressure. Thereafter, the samples were flacked on stainless steel plates, deposited with air in sealed glass containers, exposed to sunlight at ambient temperatures, opened from time to time to admit fresh air, and observed for color change. The color progression ranged from white, to yellow, to very light brown, to light brown, to brown, to dark brown, to almost black. The effective ambient white lifetime was considered finished when the samples became very light brown.

Results of the foregoing tests are presented in the Table below. The inhibitor concentrations are expressed as weight percent of the para-cresidine.

TABLE

| Sample | Inhibitor | Inhibitor Concentration (Wt. Percent) | Effective Ambient White Lifetime(Days) |
|---|---|---|---|
| 1 | None | — | 18 |
| 2 | Citric Acid | .01 | 8 |
| 3 | 2,5-Dimercapto-1,3,4-thiadiazole | .01 | 68 |
| 4 | Citric Acid + 2,5-Dimercapto-1,3,4-thiadiazole | .01 .01 | 170* |
| 5 | Hydrazine | .10 | 29 |
| 6 | Hydrazine + 2,5-Dimercapto-1,3,4-thiadiazole | .10 .01 | 89 |
| 7 | Hydrazine + Citric Acid + 2,5-Dimercapto-1,3,4-thiadiazole | .10 .01 .01 | 170* |

*The effective ambient white lifetime of these samples had not expired at the end of the data taking period.

While we have described and exemplified preferred and specific forms of our invention, alterations thereof and improvements thereon will occur to those skilled in the art without departing from the essential teachings and principles of our invention. Therefore, we do not want our patent to be restricted merely to that which is specifically disclosed herein, nor in any manner inconsistent with the progress by which the art has been promoted by our invention.

We claim:

1. A composition consisting essentially of (A) an aromatic amine of the formula R—$NH_2$ wherein R is a disubstituted phenyl radical in which one substituent is an alkoxy group of 1 to 4 carbon atoms in one of the positions ortho and para to the $NH_2$ group and the other substituent is selected from the group consisting of an alkyl group of 1 to 4 carbon atoms and a chlorine atom and is disposed in any position on the benzene ring, (B) a heterocyclic compound containing 2 to 8 carbon atoms, 2 to 3 sulfur atoms, 1 to 2 heterocyclic nitrogen atoms and at least 2 hydrogen atoms, said heterocyclic compound including a single heterocyclic ring of 5 to 6 atoms containing at least 2 carbon atoms, 1 to 2 nitogen atoms and 1 to 2 sulfur atoms, the substituents on the nitrogen atoms being restricted to hydrogen atoms and each acyclic sulfur atom being bonded to a carbon atom on the heterocyclic ring, the concentration of component (B) ranging from about 0.001 to about 0.20 percent by weight of component (A), and (C) a metal complexing agent selected from the group consisting of aliphatic, cyclicaliphatic and aromatic compounds of no more than about 22 carbon atoms and containing from two to four carboxyl groups structurally arranged to permit the hydroxyl oxygen atoms to fit the coordination positions about the metal atoms being complexed, the concentration of component (C) ranging from about 0.001 to about 0.02 percent by weight of component (A).

2. The composition of claim 1 including (D) a compound selected from the group consisting of compounds of the formula R'R''N—NH$_2$ and wherein R' and R'' are selected from the group consisting of hydrogen atoms and alkyl groups of 1 to 4 carbon atoms, the concentration of component (D) ranging from about 0.05 to about 0.5 percent by weight of component (A).

3. The composition of claim 2 wherein component (D) consists of hydrazine.

4. The composition of claim 2 wherein the concentration of component (D) ranges from about 0.05 to about 0.2 percent by weight of component (A).

5. The composition of claim 1 wherein component (A) consists of 2-methoxy-5-methyl aniline.

6. The composition of claim 1 wherein component (B) consists of 2,5-dimercapto-1,3,4-thiadiazole.

7. The composition of claim 1 wherein component (C) consists of citric acid.

8. The composition of claim 1 wherein the concentration of component (B) ranges from about 0.005 to about 0.02 percent by weight of component (A).

9. The composition of claim 1 wherein the concentration of component (C) ranges from about 0.005 to about 0.015 percent by weight of component (A).

* * * * *